United States Patent
Hsu et al.

(10) Patent No.: US 11,644,455 B2
(45) Date of Patent: May 9, 2023

(54) METHODS AND KITS FOR DETECTING SPERM DNA FRAGMENTATION

(71) Applicant: Bonraybio Co., Ltd., Taichung (TW)

(72) Inventors: Cheng-Teng Hsu, Taichung (TW); Li-Sheng Chang, Taichung (TW); Hsiu-Chin Lee, Taichung (TW)

(73) Assignee: Bonraybio Co., Ltd., Taichung (TW)

( * ) Notice: Subject to any disclaimer, the term of this patent is extended or adjusted under 35 U.S.C. 154(b) by 0 days.

(21) Appl. No.: 17/643,058

(22) Filed: Dec. 7, 2021

(65) Prior Publication Data

US 2022/0196630 A1    Jun. 23, 2022

(30) Foreign Application Priority Data

Dec. 23, 2020   (TW) .................................. 109145791

(51) Int. Cl.
*G01N 33/483*   (2006.01)
*C12N 5/076*    (2010.01)
*G01N 21/64*    (2006.01)

(52) U.S. Cl.
CPC ......... *G01N 33/4833* (2013.01); *C12N 5/061* (2013.01); *G01N 2021/6439* (2013.01)

(58) Field of Classification Search
CPC .................................................... C12N 5/061
See application file for complete search history.

(56) References Cited

U.S. PATENT DOCUMENTS

| | | | |
|---|---|---|---|
| 7,993,827 B2 * | 8/2011 | Gosalvez Berenguer | ................... C12Q 1/6827 435/6.1 |
| 8,163,481 B2 | 4/2012 | Rodriguez-Collazo et al. | |
| 9,957,548 B2 | 5/2018 | Gerdes et al. | |
| 2013/0224737 A1 | 8/2013 | Benet Catala et al. | |

FOREIGN PATENT DOCUMENTS

| CN | 101525670 A | 9/2009 |
|---|---|---|
| EP | 2637019 A1 | 9/2013 |
| EP | 2927326 B1 | 11/2018 |

OTHER PUBLICATIONS

Rosselli et al., Effect of urea and detergents on the ability of human spermatozoa to penetrate zona-free hamster oocytes, 1987, Andrologia, 570-8 (Year: 1987).*

(Continued)

*Primary Examiner* — Jennifer Wecker
*Assistant Examiner* — Mickey Huang
(74) *Attorney, Agent, or Firm* — Perkins Coie LLP; Viola T. Kung

(57) ABSTRACT

Disclosed herein are methods for the detection of the presence of sperm DNA fragmentation in a semen sample. The methods include embedding of sperm cells of the semen sample in a gel, denaturing DNA of the sperm cells, and lysing the nuclear proteins of the sperm cells. The present method includes an ionic surfactant sodium dodycyl sulfate (SDS) and a chaotropic agent urea in the lysis solution for releasing DNA from protamine of chromosome, which significantly reduces the time required for lysis. A kit for detecting sperm DNA fragmentation in a semen sample is also disclosed.

20 Claims, 3 Drawing Sheets

(56) References Cited

OTHER PUBLICATIONS

Pratap, H. et al. "Assessment of Sperm Deoxyribose Nucleic Acid Fragmentation Using Sperm Chromatin Dispersion Assay" Journal of Pharmacology and Pharmacotherapeutics; 2017; vol. 8, No. 2; pp. 45-49.
Ankem, M. et al. "Novel Assay for Determining DNA Organization in Human Spermatozoa: Implications for Male Factor Infertility" Adult Urology, 2002, vol. 59, No. 4, pp. 575-578.
Cortes-Gutierrez, E. et al. "Assessment of Sperm DNA Fragmentation in Stallion (*Equus caballus*) and Donkey (*Equus asinus*) using the Sperm Chromatin Dispersion Test" Reproduction in Domestic Animals, 2009, vol. 44, No. 5, pp. 823-828.
Enciso, M. et al. "A new method to analyze board sperm DNA fragmentation under bright-field or fluorescence microscopy" Theriogenology, 2006, vol. 65, pp. 308-316.
Extended European Search Report for European Application No. 21216691.2. dated May 24, 2022. 3 pages.
Selvam, M. et al. "A systematic review on sperm DNA fragmentation in male factor infertility: Laboratory assessment" Arab Journal of Urology, 2018, vol. 16, pp. 65-76.

\* cited by examiner

METHODS AND KITS FOR DETECTING SPERM DNA FRAGMENTATION

This application claims the priority to Taiwanese Application No:109145791, filed Dec. 23, 2020. The contents of which is incorporated herein by reference in its entirety.

FIELD

The present disclosure relates to a method for the detection of the presence of sperm DNA fragmentation in a semen sample. The present disclosure also relates to a kit for detecting sperm DNA fragmentation in a semen sample.

BACKGROUND

Sperm DNA integrity is crucial for embryo quality, embryo implantation, and embryo development. Sperm DNA fragmentation (SDF) may be caused by extrinsic factors (such as radiation, environmental pollutants, and chemotherapeutics) as well as intrinsic factors (such as defective spermatogenesis, sperm apoptosis, and oxidative stress). SDF may cause male infertility, failed in vitro fertilization (IVF), and miscarriage. Therefore, the detection of SDF is important for fertility testing and assisted reproductive techniques (ARTs).

Conventional methods for detecting SDF include sperm chromatin structure assay (SCSA), terminal deoxynucleotidyl transferase mediated dUTP nick end labeling (TUNEL) assay, DNA breakage detection-fluorescence in situ hybridization (DBD-FISH) test, comet assay (CA), and sperm chromatin dispersion (SCD) test.

SCD test is a modified halo assay that utilizes biochemical methods to detect SDF. The procedures of SCD test involve embedding sperm cells in an agarose gel, followed by DNA denaturation and deproteinization. The nuclear protein (including protamine) of each sperm cell is lysed during the deproteinization. The DNA denaturing steps takes about 7 minutes and the lysis procedure takes about 20 minutes. (see Halosperm G2 Kit product specification, Helotech)

In spite of the aforesaid, there is still a need to develop a method for rapid and accurate detection of SDF, because the more time the SCD test takes, the more specimen uncertainty the SCD test will generate.

SUMMARY

In a first aspect, the present disclosure provides a method for detecting sperm DNA fragmentation in a semen sample, which can alleviate at least one of the drawbacks of the prior art. The method includes:
(a) embedding the semen sample containing sperm cells in a gel containing a component selected from the group consisting of agarose, acrylamide, alginate, and vinyl chloride, so as to obtain a sperm cells-embedding gel;
(b) subjecting the sperm cells-embedding gel to a DNA denaturation treatment with a DNA denaturing solution, so that DNA of the sperm cells embedded in the gel is denatured;
(c) subjecting the denatured gel obtained in step (b) to a lysis treatment with a lysis solution including urea at a concentration ranging from 0.5 M to 4 M and sodium dodecyl sulfate at a concentration ranging from 0.05% (w/v, g/mL) to 0.5% (w/v, g/mL), so that nuclear proteins of the sperm cells embedded in the gel are lysed;
(d) subjecting the lysed gel obtained in step (c) to DNA staining; and
(e) observing presence or absence of halo formation around heads of the sperm cells, wherein no halo formation or presence of a halo having a halo width smaller than one third of a diameter of the corresponding head is indicative of presence of sperm DNA fragmentation.

In a second aspect, the present disclosure provides a method for detecting sperm DNA fragmentation in a semen sample, which can alleviate at least one of the drawbacks of the prior art. The method includes:
(a) subjecting an agarose solution to a heating treatment, followed by addition of a DNA denaturing solution and the semen sample containing sperm cells, so as to form a mixture;
(b) subjecting the mixture to a gel polymerization reaction, so as to obtain an agarose gel with the sperm cells containing denatured DNA embedded within;
(c) subjecting the agarose gel to a lysis treatment with a lysis solution including urea at a concentration ranging from 0.5 M to 4 M and sodium dodecyl sulfate at a concentration ranging from 0.05% (w/v, g/mL) to 0.5% (w/v, g/mL), so that nuclear proteins of the sperm cells embedded in the agarose gel are lysed;
(d) subjecting the lysed agarose gel obtained in step (c) to DNA staining; and
(e) observing presence or absence of halo formation around heads of the sperm cells, wherein no halo formation or presence of a halo having a halo width smaller than one third of a diameter of the corresponding head is indicative of presence of sperm DNA fragmentation.

In a third aspect, the present disclosure provides a method for detecting sperm DNA fragmentation in a semen sample, which can alleviate at least one of the drawbacks of the prior art. The method includes:
(a) admixing the semen sample containing sperm cells with a DNA denaturing solution and a gel-forming component, followed by subjecting a mixture thus obtained to a gel polymerization reaction, so as to obtain a gel with the sperm cells containing denatured DNA embedded within, the gel-forming component being selected from the group consisting of acrylamide, alginate, and vinyl chloride;
(b) subjecting the gel to a lysis treatment with a lysis solution including urea at a concentration ranging from 0.5 M to 4 M and sodium dodecyl sulfate at a concentration ranging from 0.05% (w/v, g/mL) to 0.5% (w/v, g/mL), so that nuclear proteins of the sperm cells embedded in the gel are lysed;
(c) subjecting the lysed gel obtained in step (b) to DNA staining; and
(d) observing presence or absence of halo formation around heads of the sperm cells, wherein no halo formation or presence of a halo having a halo width smaller than one third of a diameter of the corresponding head is indicative of presence of sperm DNA fragmentation.

In a fourth aspect, the present disclosure provides a kit for detecting sperm DNA fragmentation in a semen sample, which can alleviate at least one of the drawbacks of the prior art. The kit includes:

a gel-forming formulation which includes a component selected from the group consisting of agarose, acrylamide, alginate, and vinyl chloride;
a DNA denaturing solution;
a lysis solution including urea at a concentration ranging from 0.5 M to 4 M and sodium dodecyl sulfate at a concentration ranging from 0.05% (w/v, g/mL) to 0.5% (w/v, g/mL); and
a DNA staining reagent.

DETAILED DESCRIPTION OF THE INVENTION

Figure 1:
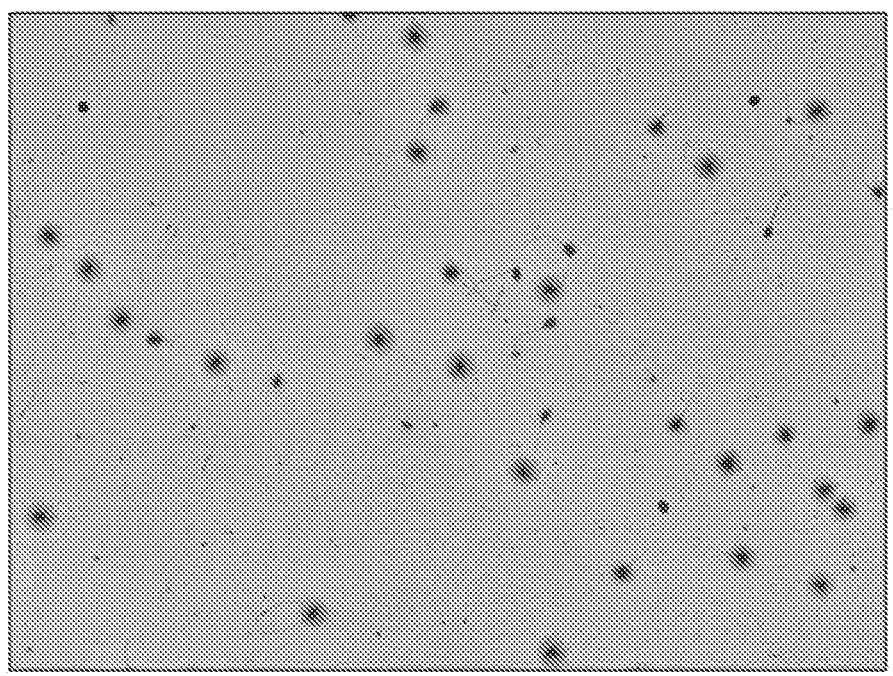
FIG. 1 shows the image of a semen sample containing sperms with halo and sperms without halo.

The present invention provides an improved method for detecting sperm DNA fragmentation in a semen sample. The inventors have discovered that by including an ionic surfactant sodium dodycyl sulfate (SDS) and a chaotropic agent urea in a lysis solution for releasing DNA from protamine of chromosome, the time required for lysis is significantly reduced.

The present disclosure provides a method for detecting sperm DNA fragmentation in a semen sample, which includes:
(a) embedding the semen sample containing semen cells in a gel comprising agarose, acrylamide, alginate, or vinyl chloride;
(b) subjecting the sperm cells-embedding gel to a DNA denaturation treatment with a DNA denaturing solution, to denature the DNA of the sperm cells;
(c) subjecting the denatured gel obtained in step (b) to a lysis treatment with a lysis solution including urea at a concentration ranging from 0.5 M to 4 M and sodium dodecyl sulfate at a concentration ranging from 0.05% (w/v, g/mL) to 0.5% (w/v, g/mL) to lyse the nuclear proteins of the sperm cells;
(d) subjecting the lysed gel obtained in step (c) to DNA staining; and
(e) observing the presence or the absence of halo formation around heads of the sperm cells, wherein no halo formation or the presence of a halo having a halo width smaller than one third of a diameter of the corresponding sperm head is indicative of presence of sperm DNA fragmentation.

According to the present disclosure, in step (a), the gel optionally further contains an acid-base indicator selected from the group consisting of phenol red, methyl violet, methyl orange, methyl red, Congo red, and combinations thereof. In certain embodiments, the acid-base indicator is phenol red.

In certain embodiments, in step (a), the gel may be an agarose gel.

According to the present disclosure, the agarose gel may have an agarose concentration ranging from 1% (w/v, g/mL) to 3% (w/v, g/mL). In an exemplary embodiment, the agarose gel has an agarose concentration of 1.25% (w/v, g/mL).

According to the present disclosure, prior to use for embedding the semen sample, the agarose gel may be melted at a temperature ranging from 95° C. to 100° C. using a microwave oven or a constant temperature water bath. In an exemplary embodiment, the agarose gel is melted at a temperature of 95° C.

According to the present disclosure, the semen sample may be collected from a male subject at any time. In an exemplary embodiment, the semen sample is collected from a male subject who has experienced sexual abstinence for at least 2 to 3 days but not greater than 10 days.

According to the present disclosure, the semen sample may be fresh or frozen (e.g., may be in a frozen form stored in liquid nitrogen (−196° C.)

As used herein, the term "subject" refers to any animal of interest, such as primates (e.g., humans, apes, and monkeys), non-primate mammals (e.g., pigs, cows, sheep, horses, goats, dogs, cats, mice, and rats), fish, and amphibians. In certain embodiments, the subject is a mammal or a human.

According to the present disclosure, the semen sample may be diluted with a diluent to have a sperm concentration ranging from of $4 \times 10^6$ cells/mL to $1.5 \times 10^7$ cells/mL.

Examples of the diluent may include, but are not limited to, Earle's medium, human tubal fluid (HTF) medium, Tris-buffered saline (TBS), phosphate-buffered saline (PBS), and saline.

In certain embodiments, the semen sample is diluted with HTF medium to have a sperm concentration of $1 \times 10^7$ cells/mL.

According to the present disclosure, the DNA denaturing solution may be an acidic aqueous solution or an alkaline aqueous solution, and may have an equivalent concentration ranging from 0.05 N to 0.08 N. In certain embodiments, the DNA denaturing solution may have an equivalent concentration ranging from 0.06 N to 0.07 N.

According to the present disclosure, the DNA denaturing solution may be an acidic aqueous solution containing an acid selected from the group consisting of hydrochloric acid, acetic acid, nitric acid, sulfuric acid, and combinations thereof. In certain embodiments, the DNA denaturing solution is an acidic aqueous solution containing hydrochloric acid.

According to the present disclosure, the DNA denaturing solution may be an alkaline aqueous solution containing a base selected from the group consisting of sodium hydroxide, potassium hydroxide, calcium hydroxide, and combinations thereof. In certain embodiments, the DNA denaturing solution is an alkaline aqueous solution containing sodium hydroxide.

As used herein, the term "lysis solution" can be used interchangeably with the terms "cell lysis solution" and "protein lysis solution."

According to the present disclosure, in the lysis solution, sodium lauryl sulfate, also referred to as sodium dodecyl sulfate (SDS) is used as an ionic surfactant, and urea is used as a protein denaturant. These two components improve the lysis of protamine and thus the DNA loops can be easily released from the protamine to the periphery of the head of the sperm cell, and then be monitored as a halo via DNA staining. The inventors discover that using SDS and urea in the lysis solution effectively reduces the time of lysis treatment (for example, to less than 5 minutes) and thus reducing the specimen uncertainty.

According to the present disclosure, the lysis solution may further include an additional ionic or nonionic surfactant.

In certain embodiments, the additional ionic surfactant may be selected from the group consisting of sodium deoxycholate, sodium cholate, sodium lauroyl sarcosinate, and combinations thereof.

In certain embodiments, the additional nonionic surfactant may be selected from the group consisting of Triton X-100, Nonoxynol-40 (NP-40), Pluronic F-127 (F-127), Tween-20, and combinations thereof. In an exemplary embodiment, the additional nonionic surfactant is Triton X-100.

According to the present disclosure, the lysis solution may further include an additional protein denaturant. Examples of the additional protein denaturant may include, but are not limited to, 3-[(3-cholamidopropyl)dimethylammonio]-1-propanesulfonate hydrate, guanidinium chloride, and a combination thereof.

According to the present disclosure, the lysis solution may further include a reducing agent. Examples of the reducing agent may include, but are not limited to, dithiothreitol (DTT), tris(2-carboxyethyl)phosphine (TCEP) hydrochloride, dithioerythritol (DTE), β-mercaptoethanol (β-ME), glutathione (GSH), dimercaprol, heparin, and combinations thereof. In an exemplary embodiment, the reducing agent is DTT or TCEP.

According to the present disclosure, the lysis solution may further include salts. Examples of the salts may include, but are not limited to, sodium chloride (NaCl), potassium chloride (KCl), and a combination thereof.

According to the present disclosure, the lysis solution may further include a pH titrant. Examples of the titrant may include, but are not limited to, sodium hydroxide (NaOH), hydrochloric acid (HCl), and a combination thereof.

In certain embodiments, the lysis solution may further include 0.15 M to 3 M of NaCl, 0.05 M to 0.2 M of DTT or TCEP, 0.1% (v/v) to 5% (v/v) of Triton X-100, and 0.01 M to 0.02 M of NaOH.

In an exemplary embodiment, the lysis solution includes 1 M urea, 0.05% (w/v, g/mL) of SDS, 2.5 M NaCl, 0.1 M DTT or 0.05 M TCEP, 1% (v/v) of Triton X-100, and 0.02 M NaOH. In another exemplary embodiment, the lysis solution includes 4 M urea, 0.05% (w/v, g/mL) of SDS, 0.15 M NaCl, 0.2 M DTT or 0.05 M TCEP, 0.5% (v/v) of Triton X-100, and 0.01 M NaOH. In yet another exemplary embodiment, the lysis solution includes 0.5 M urea, 0.5% (w/v, g/mL) of SDS, 3 M NaCl, 0.05 M DTT or TCEP, 5% (v/v) of Triton X-100, and 0.015 M NaOH.

According to the present disclosure, the lysis solution may be adjusted to have a desired pH value using the titrant. In certain embodiments, when the DNA denaturing solution is an acidic aqueous solution, the lysis solution may have a pH value ranging from 7.5 to 9.0. In certain embodiments, when the DNA denaturing solution is an alkaline aqueous solution, the lysis solution may have a pH value ranging from 5.5 to 7.0. In an exemplary embodiment, the lysis solution has a pH value ranging from 8.2 to 8.5.

According to the present disclosure, the DNA staining is conducted using a staining method selected from the group consisting of Diff-Quik staining, Wright-Giemsa staining, propidium iodide (PI) staining, SYBR Green staining, 4',6-diamidino-2-phenylindole (DAPI) staining, and acridine orange staining.

The present disclosure also provides another method for detecting sperm DNA fragmentation in a semen sample, which includes:
(a) subjecting an agarose solution to heat, followed by addition of a DNA denaturing solution and the semen sample containing semen cells, so as to form a mixture;
(b) subjecting the mixture to a gel polymerization reaction, so as to obtain an agarose gel with the sperm cells containing denatured DNA embedded within;
(c) subjecting the agarose gel to lysis with a lysis solution including urea at a concentration ranging from 0.5 M to 4 M and sodium dodecyl sulfate at a concentration ranging from 0.05% (w/v, g/mL) to 0.5% (w/v, g/mL), so that nuclear proteins of the sperm cells embedded in the agarose gel are lysed;
(d) subjecting the lysed agarose gel obtained in step (c) to DNA staining; and
(e) observing the presence or the absence of halo formation around heads of the sperm cells, wherein no halo formation or the presence of a halo having a halo width smaller than one third of a diameter of the corresponding head is indicative of presence of sperm DNA fragmentation.

According to the present disclosure, in step (a), the agarose solution may be further admixed with an acid-base indicator as described above before the heat treatment.

According to the present disclosure, the heat treatment may be conducted at a temperature ranging from 95° C. to 100° C. In an exemplary embodiment, the heating treatment is conducted at a temperature of 95° C.

The details of the operating conditions and reagents (i.e., the preparation of the semen sample, the DNA denaturing solution, the lysis solution, the DNA staining method, etc.) of another method are generally the same as those described above.

In addition, the present disclosure further provides yet another method for detecting sperm DNA fragmentation in a semen sample, which includes:
(a) admixing the semen sample containing sperm cells with a DNA denaturing solution and a gel-forming component, followed by subjecting a mixture thus obtained to a gel polymerization reaction, so as to obtain a gel with the sperm cells containing denatured DNA embedded within, the gel-forming component being selected from the group consisting of acrylamide, alginate, and vinyl chloride;
(b) subjecting the gel to lysis with a lysis solution including urea at a concentration ranging from 0.5 M to 4 M and sodium dodecyl sulfate at a concentration ranging from 0.05% (w/v, g/mL) to 0.5% (w/v, g/mL), so that nuclear proteins of the sperm cells embedded in the gel are lysed;
(c) subjecting the lysed gel obtained in step (b) to DNA staining; and
(d) observing the presence or the absence of halo formation around heads of the sperm cells, wherein no halo formation or the presence of a halo having a halo width smaller than one third of a diameter of the corresponding head is indicative of presence of sperm DNA fragmentation.

According to the present disclosure, in step (a), the mixture may be further admixed with an acid-base indicator as described above before the gel polymerization reaction.

The details of the operating conditions and reagents (i.e., the preparation of the semen sample, the DNA denaturing solution, the lysis solution, the DNA staining method, etc.) of the yet another method are generally the same as those described above.

In the present methods, the images of the halo formation can be studied by direct visual analysis with a microscope or by applying digitalized images analysis software, obtained by using analogue or digital cameras, coupled to the microscope platforms.

In all the present methods described above, after the step of observing the presence or the absence of halo formation around heads of the sperm cells, optionally the methods further comprise a step of calculating DNA fragmentation index (DFI) (%), which is the % of number of sperms with DNA fragmentation over the total number of sperms. In general, normal semen samples have DFI≤15%; abnormal semen samples have DFI≥30%. In between (15%<DFI<30%) are considered borderline samples or threshold sample.

FIG. 1 shows an image of sperms with a halo formation and sperms without a halo formation, around heads of the sperms, in a threshold semen sample.

In another aspect, the present disclosure provides a kit for detecting sperm DNA fragmentation in a semen sample, which includes:

a gel-forming formulation which includes a component selected from the group consisting of agarose, acrylamide, alginate, and vinyl chloride;

a DNA denaturing solution;

a lysis solution including urea at a concentration ranging from 0.5 M to 4 M and sodium dodecyl sulfate at a concentration ranging from 0.05% (w/v, g/mL) to 0.5% (w/v, g/mL); and a DNA staining reagent.

In certain embodiments, the component is agarose.

In certain embodiments, the component is acrylamide.

In certain embodiments, the gel-forming formulation includes an acrylamide/bis-acrylamide solution.

According to the present disclosure, the gel-forming formulation may further include an initiator.

In certain embodiments, the acrylamide/bis-acrylamide solution and the initiator are placed in separate containers (such as, microcentrifuge tubes, glass bottles or plastic bottles).

According to the present disclosure, the initiator may be selected from the group consisting of ammonium persulfate (APS), tetramethylethylenediamine (TEMED), riboflavin-5'-phosphate sodium, 3-(dimethylamino)propionitrile, and combinations thereof.

According to the present disclosure, the gel-forming formulation may further include an acid-base indicator as described above.

The details of the reagents (i.e., the DNA denaturing solution and the lysis solution) applied in this kit are generally the same as those described above.

In certain embodiments, the DNA denaturing solution and the gel-forming formulation are placed in separate containers (such as, microcentrifuge tubes, glass bottles or plastic bottles).

According to the present disclosure, the kit may further include a support for carrying the semen sample. The support includes a support base and an agarose layer disposed on a surface of the support base, and the agarose layer has an agarose concentration ranging from 0.25% (w/v, g/L) to 1.5% (w/v, g/L).

Examples of the support base may include, but are not limited to, a microscope slide and a well-plate.

In an exemplary embodiment, the support base is a microscope slide, and a surface of the microscope slide has been overlaid with a layer of 1% (w/v, g/L) of agarose.

According to the present disclosure, the DNA staining reagent may be selected from the group consisting of Diff-Quik solution, Wright-Giemsa solution, PI, SYBR Green, DAPI, and acridine orange.

The disclosure will be further described by way of the following examples. However, it should be understood that the following examples are solely intended for the purpose of illustration and should not be construed as limiting the disclosure in practice.

EXAMPLES

Test Lysis Solution

The Test Lysis Solution used in the following experiments for Test Samples contained 2.5 M sodium chloride (NaCl), 0.2 M dithiothreitol (DTT), 4 M urea, 1% Triton X-100, 0.05% sodium dodecyl sulfate (SDS), and 0.01 M sodium hydroxide (NaOH), and had a pH value ranging from 8.2 to 8.5.

Conventional Lysis Solution

The Conventional Lysis Solution used in the following experiments for control samples contained 2.5 M NaCl, 0.2 M DTT, 0.2 M Tris, and 1% Triton X-100. This Conventional Lysis Solution is used in the sperm chromatin dispersion (SCD) test.

Example 1. Evaluation of Various Lysis Solutions on Sperm DNA Fragmentation (SDF)

Experimental Procedures

A semen sample of male Subject 1 (age between 22-40 years old) was collected, followed by liquefaction at room temperature. 100 µL of the liquefied semen sample was subjected to determination of the number of sperm cells using a semen quality analyzer (X1 PRO, LensHooke) in accordance with the manufacturer's instructions. Afterwards, a suitable amount of phosphate-buffered saline (PBS) was added to dilute the semen sample to reach a sperm cell concentration of $0.1 \times 10^5$ cells/µL. Five aliquots (25 µL each) of the diluted semen suspension of Subject 1 were used for the following experiments.

One aliquot served as a control sample, and the other four aliquots respectively served as four test samples (i.e., test sample 1 to 4). Each aliquot was added with 100 µL of a pre-heated agarose solution (1.25% (w/v, g/L), in $H_2O$; Uniregion Bio Tech Inc.) containing 0.02 mg/mL phenol red. 25 µL of the respective resultant mixture was placed on an agarose layer (containing 1% (w/v, g/L) agarose) disposed on a surface of a microscope slide, followed by being left standing at 4° C. for 5 minutes, such that the sperm cells were embedded in an agarose gel and were immobilized on the microscope slide. The sperm cells-embedding agarose gel (AG) was subjected to the following DNA hydrolysis treatment and is referred to as "sperm cells-AG" hereinafter.

The sperm cells-AG of each control sample and test samples was treated with 200-300 µL of a DNA denaturing solution containing 0.1 N HCl, followed by being left standing for reaction to proceed at room temperature for 7 minutes.

The denatured sperm cells-AG of the test samples 1-4 were treated with 200-300 µL of a Test Lysis Solution as described above at room temperature for 2 minutes, 5 minutes, 10 minutes, and 20 minutes, respectively. Separately, the denatured sperm cells-AG of the control sample was treated with 200-300 µL of a Conventional Lysis Solution, at room temperature for 20 minutes.

After washing with water two times, the lysed sperm cells-AG of the respective sample was subjected to dehydration using 70% ethanol, followed by conducting Wright-Giemsa staining using a staining protocol well-known to those skilled in the art. The resultant stained sperm cells-AG was then observed and photographed under an optical microscope (BX-53, Olympus) at 100× and 200× magnifications.

The number of sperm cells with no halo or with a halo having a halo width smaller than one third of the diameter of the sperm head (i.e., the number of sperm cells with DNA fragmentation) was calculated, and the DNA fragmentation index (DFI) (%) of each sample was further calculated using a technique well known to those skilled in the art.

Results

Figure 2:
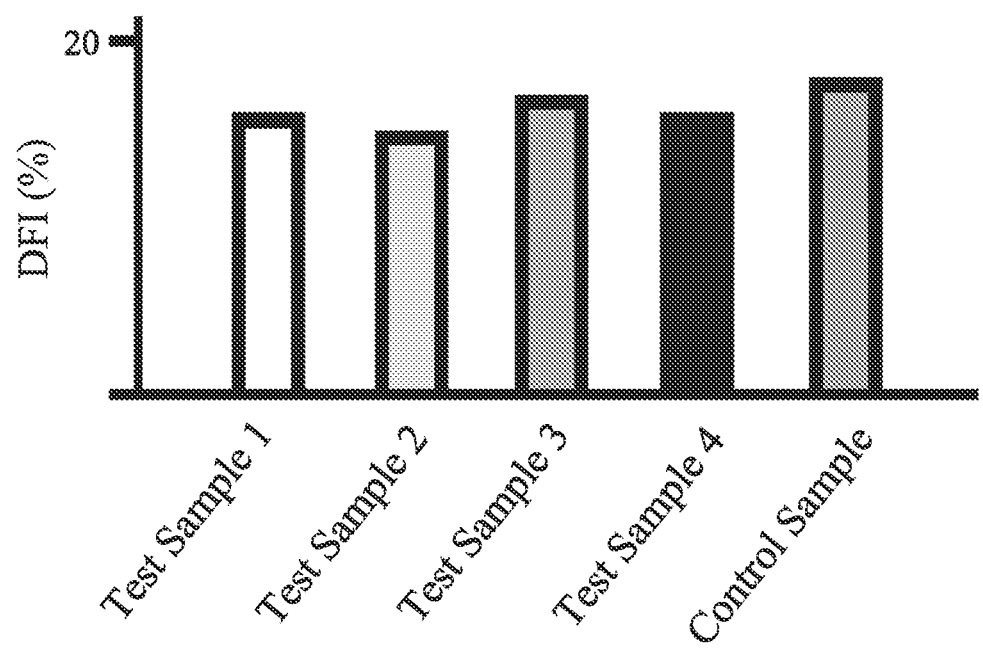
FIG. 2 shows the DNA fragmentation index (DFI) determined in each test sample and control sample of Example 1.

Referring to FIG. 2, no significant difference was observed on the DFI among the test samples 1 to 4 and the control sample. The results demonstrate that use of a lysis solution containing urea and SDS for lysing sperm cells effectively accelerate the lysis of sperm nuclear proteins, and hence can shorten the detection time and exhibit a detection effect similar to that of the conventional method (e.g., the SCD test).

Example 2. Effect of Pretreatment of Semen Suspension with DNA Denaturing Solution on the Detection of SDF Experimental Procedures A semen sample of male Subject 2 (age between 22-40 years old) was collected. Three aliquots were prepared according to Example 1. One aliquot served as a control sample, and the other two aliquots respectively served as Test Samples 1 to 2.

The control sample was subjected to detection of SDF according to the method as described in Example 1, and the DFI was calculated using a technique well known to those skilled in the art.

Test Sample 1 was subjected to detection of SDF according to the method similar to that performed for Test sample 2 as described in Example 1, and the DFI was calculated using a technique well known to those skilled in the art.

Test Sample 2 was subjected to detection of SDF according to the following operating procedures. First, 50 μL of a pre-heated agarose solution (1.25% (w/v, g/L), in $H_2O$; Uniregion Bio Tech Inc.) containing 0.02 mg/mL phenol red was mixed with 25 μL of a DNA denaturing solution containing 0.28 N HCl, followed by mixing with the test sample 2. The resultant mixture was placed on an agarose layer (containing 1% (w/v, g/L) agarose) disposed on a surface of a microscope slide, followed by being left standing at 4° C. for 6 minutes, such that the denatured sperm cells were embedded in an agarose gel and were immobilized on the microscope slide. The resultant denatured sperm cells-embedding agarose gel (AG) is referred to as "denatured sperm cells-AG" hereinafter.

Thereafter, the denatured sperm cells-AG of the Test Sample 2 was treated with 200-300 μL of a Test Lysis Solution as described in Example 1 at room temperature for 5 minutes. After washing with water two times, the lysed sperm cells-AG was subjected to dehydration using 70% ethanol, followed by conducting Wright-Giemsa staining using a staining protocol well-known to those skilled in the art. The resultant stained sperm cells-AG was then observed and photographed under an optical microscope (BX-53, Olympus) at 100× and 200× magnifications. The number of sperm cells with DNA fragmentation was calculated according to the method described in Example 1, and the DFI was further calculated using a technique well known to those skilled in the art.

Results

As shown in Table 1 below, no significant difference was observed on the DFI among the Test Sample 1 to 2 and the control sample. The result indicates that the Test Lysis Solution containing urea and SDS can shorten the detection time, with or without pretreatment of the semen suspension with a DNA denaturing solution, and can exhibit a detection effect similar to that of the conventional method (e.g., the SCD test).

TABLE 1

| Sample | Lysis solution | Lysis time (mins) | pretreatment of a semen suspension with a DNA denaturing solution | DFI (%) |
|---|---|---|---|---|
| Control | Without Urea & SDS | 20 | No | 19 |
| Test 1 | With Urea & SDS | 5 | No | 18 |
| Test 2 | With Urea & SDS | 5 | Yes | 19 |

Example 3. Effect of Lysis Time of Semen Suspension on the Detection of SDF

Experimental Procedures

A semen sample of male Subject 3 (age between 22-40 years old) was collected. Eight aliquots were prepared according to Example 1. Four aliquots served as Test Samples 1-4, and the other four aliquots served as Control Samples 1-4.

The four Test Samples were subjected to detection of SDF according to the method similar to that performed for Test sample 1 as described in Example 2 (with Test Lysis Solution containing urea and SDS), except the lysis time of each Test Sample is different (see Table 2).

The four Control Samples were subjected to detection of SDF according to the method as described in Example 2 (with Conventional Lysis Solution without urea and SDS), except the lysis time of each Test Sample is different (see Table 2).

The DFI (%) results are shown in Table 2. The results show that when including urea and SDS in a lysis solution, the lysis time could be shortened from 20 minutes to 2 minutes to achieve the same DFI results. On the contrary, the conventional lysis solution required 20 minutes to completely lyse the nuclear proteins of the sperm cells embedded in the gel and to achieve correct DFI results. Shorter lysis time of 2, 5, or 10 minutes with the conventional lysis solution without urea and SDS did not completely lyse the nuclear proteins of the sperm cells embedded in the gel and did not achieve correct DFI results.

TABLE 2

| | Sample | Lysis solution | Lysis time (mins) | DFI (%) |
|---|---|---|---|---|
| Test samples | Test 1 | With urea & SDS | 2 | 10 |
| | Test 2 | With urea & SDS | 5 | 9 |
| | Test 3 | With urea & SDS | 10 | 9 |
| | Test 4 | With urea & SDS | 20 | 8 |

TABLE 2-continued

|  | Sample | Lysis solution | Lysis time (mins) | DFI (%) |
|---|---|---|---|---|
| Control samples | Control 1 | Without urea & SDS | 2 | 23 |
|  | Control 2 | Without urea & SDS | 5 | 18 |
|  | Control 3 | Without urea & SDS | 10 | 14 |
|  | Control 4 | Without urea & SDS | 20 | 9 |

Example 4. Evaluation for the Accuracy of Method of Present Disclosure

Experimental Procedures 22 semen samples from male Subjects (age between 22-40 years old) were collected and diluted semen suspensions were prepared according to Example 1. The diluted semen suspensions were subjected to detection of SDF according to the method similar to that performed for test sample 2 as described in Example 2, and the DFI of the respective test semen suspension was calculated using a technique well known to those skilled in the art.

In addition, the 22 test semen suspensions were also subjected to the SCD test, and the operating procedures of the SCD test were similar to those performed for the control sample as described in Example 1.

The DFIs respectively determined based on the method of the present disclosure and the SCD test were then analyzed using linear regression and Pearson's correlation analysis to determine the correlation therebetween, and a coefficient of determination ($R^2$ value) was calculated.

Results

Figure 3:
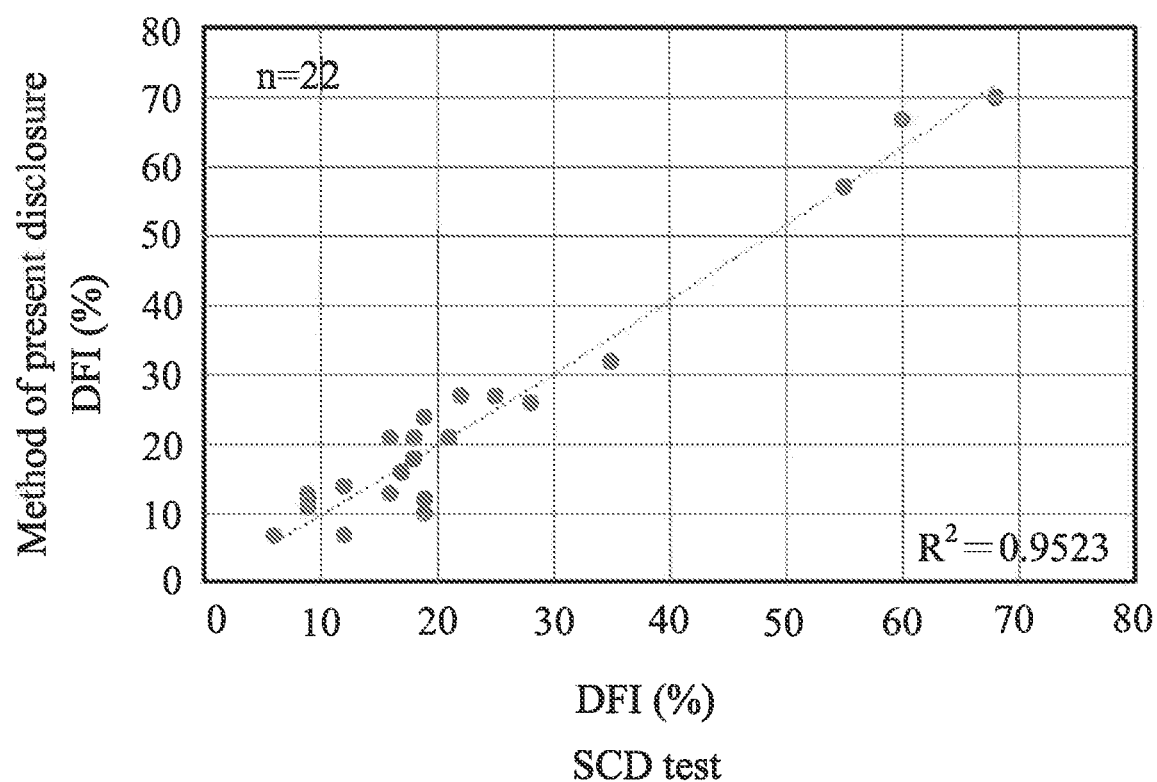
FIG. 3 shows a correlation plot of 22 semen samples between the DFI determined according to the present method and the DFI determined according to sperm chromatin dispersion (SCD) test.

Referring to FIG. 3, the DFI determined according to the method of the present disclosure and the DFI determined according to the SCD test had an excellent correlation therebetween, with a calculated $R^2$ value of 0.9523. The result indicates that the accuracy of the method of the present disclosure is the same as that of the SCD test.

Summarizing the test results above, the present method can effectively detect sperm DNA fragmentation in a semen sample, and hence is useful for evaluating male infertility.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for detecting sperm DNA fragmentation in a semen sample, comprising:
   (a) embedding the semen sample containing semen cells in a gel comprising agarose, acrylamide, alginate, or vinyl chloride;
   (b) subjecting the sperm cells-embedding gel to a DNA denaturation treatment with a DNA denaturing solution, to denature the DNA of the sperm cells;
   (c) subjecting the denatured gel obtained in step (b) to a lysis treatment with a lysis solution including urea at a concentration ranging from 0.5 M to 4 M and sodium dodecyl sulfate at a concentration ranging from 0.05% (w/v, g/mL) to 0.5% (w/v, g/mL) to lyse the nuclear proteins of the sperm cells;
   (d) subjecting the lysed gel obtained in step (c) to DNA staining; and
   (e) observing the presence or the absence of halo formation around heads of the sperm cells, wherein no halo formation or the presence of a halo having a halo width smaller than one third of a diameter of the corresponding sperm head is indicative of presence of sperm DNA fragmentation.

2. The method of claim 1, wherein in step (a), the gel further contains an acid-base indicator selected from the group consisting of phenol red, methyl violet, methyl orange, methyl red, Congo red, and combinations thereof.

3. The method of claim 1, wherein the DNA denaturing solution is an acidic aqueous solution containing an acid selected from the group consisting of hydrochloric acid, acetic acid, nitric acid, sulfuric acid, and combinations thereof.

4. The method of claim 1, wherein the DNA denaturing solution is an alkaline aqueous solution containing sodium hydroxide, potassium hydroxide, calcium hydroxide, or a combination thereof.

5. The method of claim 1, wherein the lysis solution further includes a protein denaturant of 3-[(3-cholamidopropyl)dimethylammonio]-1-propanesulfonate hydrate, guanidinium chloride, or a combination thereof.

6. The method of claim 1, wherein the lysis solution further includes an ionic surfactant selected from the group consisting of sodium deoxycholate, sodium cholate, sodium lauroyl sarcosinate, and combinations thereof.

7. A method for detecting sperm DNA fragmentation in a semen sample, comprising:
   (a) heating an agarose solution, followed by adding a DNA denaturing solution and a semen sample containing sperm cells to the heated agarose solution to form a mixture;
   (b) subjecting the mixture to a gel polymerization reaction, to obtain an agarose gel with the sperm cells containing denatured DNA embedded within;
   (c) subjecting the polymerized agarose gel to a lysis treatment with a lysis solution comprising 0.5 M to 4 M urea and 0.05% to 0.5% (w/v) sodium dodecyl sulfate to lyse the nuclear proteins of the sperm cells embedded in the agarose gel;
   (d) subjecting the lysed agarose gel obtained in step (c) to DNA staining; and
   (e) observing the presence or the absence of halo formation around heads of the sperm cells, wherein no halo formation or the presence of a halo having a halo width smaller than one third of a diameter of the corresponding sperm head is indicative of presence of sperm DNA fragmentation.

8. The method of claim 7, wherein in step (a), the agarose solution is further admixed with an acid-base indicator before the heating treatment, the acid-base indicator being selected from the group consisting of phenol red, methyl violet, methyl orange, methyl red, Congo red, and combinations thereof.

9. The method of claim 7, wherein the DNA denaturing solution is an acidic aqueous solution containing an acid selected from the group consisting of hydrochloric acid, acetic acid, nitric acid, sulfuric acid, and combinations thereof.

10. The method of claim 7, wherein the DNA denaturing solution is an alkaline aqueous solution containing sodium hydroxide, potassium hydroxide, calcium hydroxide, or combinations thereof.

11. The method of claim 7, wherein the lysis solution further includes a protein denaturant of 3-[(3-cholamidopropyl)dimethylammonio]-1-propanesulfonate hydrate, guanidinium chloride, or a combination thereof.

12. The method of claim 7, wherein the lysis solution further includes an ionic surfactant selected from the group consisting of sodium deoxycholate, sodium cholate, sodium lauroyl sarcosinate, and combinations thereof.

13. A method for detecting sperm DNA fragmentation in a semen sample, comprising:
   (a) admixing a semen sample containing sperm cells with a DNA denaturing solution and a gel-forming component, followed by subjecting a mixture thus obtained to a gel polymerization reaction, so as to obtain a gel with the sperm cells containing denatured DNA embedded within, the gel-forming component being selected from the group consisting of acrylamide, alginate, and vinyl chloride;
   (b) subjecting the gel to a lysis treatment with a lysis solution including 0.5 M to 4 M urea and 0.05% to 0.5% (w/v) sodium dodecyl sulfate, to lyse the nuclear proteins of the sperm cells embedded in the gel;
   (c) subjecting the lysed gel obtained in step (b) to DNA staining; and
   (d) observing the presence or the absence of halo formation around heads of the sperm cells, wherein no halo formation or the presence of a halo having a halo width smaller than one third of a diameter of the corresponding sperm head is indicative of presence of sperm DNA fragmentation.

14. The method of claim 13, wherein in step (a), the mixture is further admixed with an acid-base indicator before the gel polymerization reaction, the acid-base indicator being selected from the group consisting of phenol red, methyl violet, methyl orange, methyl red, Congo red, and combinations thereof.

15. The method of claim 13, wherein the DNA denaturing solution is an acidic aqueous solution containing an acid selected from the group consisting of hydrochloric acid, acetic acid, nitric acid, sulfuric acid, and combinations thereof.

16. The method of claim 13, wherein the DNA denaturing solution is an alkaline aqueous solution containing a base selected from the group consisting of sodium hydroxide, potassium hydroxide, calcium hydroxide, and combinations thereof.

17. The method of claim 13, wherein the lysis solution further includes a protein denaturant of 3-[(3-cholamidopropyl)dimethylammonio]-1-propanesulfonate hydrate, guanidinium chloride, or a combination thereof.

18. The method of claim 13, wherein the lysis solution further includes an ionic surfactant selected from the group consisting of sodium deoxycholate, sodium cholate, sodium lauroyl sarcosinate, and combinations thereof.

19. A kit for detecting sperm DNA fragmentation in a semen sample, comprising:
   a gel-forming formulation comprising agarose, acrylamide, alginate, or vinyl chloride;
   a DNA denaturing solution;
   a lysis solution having 0.5 M to 4 M of urea and 0.05% to 0.5% (w/v) sodium dodecyl sulfate; and
   a DNA staining reagent.

20. The kit of claim 19, wherein the gel-forming formulation further includes an acid-base indicator selected from the group consisting of phenol red, methyl violet, methyl orange, methyl red, Congo red, and combinations thereof.

* * * * *